United States Patent [19]

Amkraut et al.

[11] 4,439,199

[45] Mar. 27, 1984

[54] METHOD FOR ADMINISTERING IMMUNOPOTENTIATOR

[75] Inventors: Alfred A. Amkraut; Agusto B. Martins, both of Palo Alto, Calif.

[73] Assignee: Alza Corporation, Palo Alto, Calif.

[21] Appl. No.: 361,895

[22] Filed: Mar. 25, 1982

Related U.S. Application Data

[63] Continuation-in-part of Ser. No. 122,124, Feb. 19, 1980.

[51] Int. Cl.³ .............................................. A61L 15/06
[52] U.S. Cl. ..................................... 604/894; 604/897
[58] Field of Search .................. 128/890, 260, 207.21, 128/155, 156; 424/19-26; 604/890, 891, 892, 893, 894, 895, 896, 897

[56] References Cited

U.S. PATENT DOCUMENTS

| | | | |
|---|---|---|---|
| 2,332,521 | 10/1943 | Masucci | 167/78 |
| 3,075,883 | 1/1963 | Scherr et al. | 167/78 |
| 3,135,662 | 6/1964 | Pope et al. | 167/78 |
| 3,452,135 | 6/1969 | Medveczky | 424/9 |
| 3,493,652 | 2/1970 | Hartman | 424/9 |
| 3,522,347 | 7/1970 | Ablondi et al. | 424/92 |
| 3,678,149 | 7/1972 | Prigal | 424/88 |
| 3,752,886 | 8/1973 | Munder et al. | 424/199 |
| 3,767,790 | 10/1973 | Guttag | 424/81 |
| 3,787,571 | 1/1974 | Higuchi | 424/239 |
| 3,814,097 | 6/1974 | Ganderton et al. | 128/268 |
| 3,837,340 | 9/1974 | Counter | 128/260 |
| 3,859,435 | 1/1975 | Bruzzese et al. | 424/94 |
| 3,867,519 | 2/1975 | Michaels | 424/19 |
| 3,937,815 | 2/1976 | Bruzzese et al. | 424/94 |
| 3,964,482 | 6/1976 | Gerstel et al. | 128/260 |
| 3,995,631 | 12/1976 | Higuchi et al. | 128/260 |

*Primary Examiner*—C. Fred Rosenbaum
*Assistant Examiner*—T. J. Wallen
*Attorney, Agent, or Firm*—Paul L. Sabatine; Edward L. Mandell

[57] ABSTRACT

The invention pertains to the administration of an immunopotentiator to activate an immune response. The administration comprises the controlled and continuous administration of the immunopotentiator leading to a high immune response with adequate persistancy, while simultaneously and substantially reducing or eliminating inflammatory reactions usually accompanying depot-type administration.

21 Claims, No Drawings

METHOD FOR ADMINISTERING IMMUNOPOTENTIATOR

CROSS-REFERENCE TO RELATED APPLICATIONS

This application is a continuation-in-part of U.S. patent application Ser. No. 06/122,124 filed on Feb. 19, 1980, which application is incorporated herein by reference and benefit is claimed of its filing date. This application is copending with applicants' U.S. patent application Ser. No. 06/069,733 and titled "A Method of Coadministering an Antigen and an Immunopotentiator". These applications are assigned to the ALZA Corporation of Palo Alto, Calif.

FIELD OF INVENTION

This invention pertains to the immunological competence of a host, and more particularly, to a method for activating the immune response of a host. Specifically, the invention concerns a method comprising administering continuously an immunopotentiator at a controlled rate over time for enhancing the immune response against an impending infection, a disease in progress, or in an immunodepressed state.

BACKGROUND OF THE INVENTION

In the prior art, it is desirable to administer an immunopotentiator for activating the immune response of a host as prophylaxis against an impending infection, for the management of a disease in progress, to potentiate the immune response against tumor cells, or for restoring the immune response in immunodepressed states. Generally, the immunopotentiators are used to enhance the immune system including, but are not limited to, increasing macrophage activity, improving T cell response, increasing NK cell activity, increasing B cell response, increasing complement activity, inducing interferon production, increasing granulocyte function, and the like.

The immunopotentiators of the prior art administered to a host for stimulating the immune response broadly include immunopotentiators of synthetic origin, immunopotentiators of natural origin, and immunopotentiators derived from biological sources. While the use of immunopotentiators represents a valuable contribution to the prior art, serious disadvantages often are associated with their use. For example, while one of the aims of using an immunopotentiator is to activate and achieve an immune response of a durable and high level, the immunopotentiator in many instances quickly dissipates necessitating a number of repeated doses, for example, as practiced in the management of neoplastic diseases, for producing the intended results. Another shortcoming frequently observed is the administration of the immunopotentiator in a single and repeated doses does not supply enough immunopotentiator for stimulating the immune system, and the immunopotentiator administered often causes toxic effects such as fever, malaise, and the like.

In other embodiments the prior art resorted to carriers, such as oily emulsions in depot form for administering the immunopotentiator for obtaining the desired benefit, but this too entailed drawbacks. For example, the oils used are not easily metabolized, they may be incompatible with the host, and they can give rise to sever toxic reactions. These affects tend to defeat their use. Then too, the previous methods of administration expose the tissues of the host to unknown quantities of immunopotentiator which can be irritating and react with the tissue, producing an unwanted inflammatory response that is of unknown severity and duration. The use of oily depots, which are not immunopotentiators, but are intended to function as an in vivo repository, are replete with shortcomings. That is, depots do not keep their integrity and accordingly they do not maintain a predictable repository effect. By losing their integrity, they allow large numbers of inflammatory cells to accumulate at the depot site thereby producing unwanted irritation and often granulamatous lesions. Depots previously known to the art are made of materials that spread and diffuse throughout the area in which they are injected and they are not conducive for the controlled release of immunopotentiator over time.

It will be appreciated by those versed in the art that if a method is made available for delivering an immunopotentiator to enhance the immune response, which method is free of the high single dose or the multiple dose disadvantages known to the prior art, such a method would represent a valuable contribution to the art. Likewise, it will be appreciated by those versed in the art, that if a method is made available which avoids giving rise to significant local inflammation, such a method also would be a useful contribution to the art. Similarly, it will be appreciated that if a method is provided which accelerates the appearance of the immune response at protective levels, such a method would also be an improvement in the art.

OBJECTS OF THE INVENTION

Accordingly, it is an immediate object of the present invention to provide a novel and useful immunologic program for administering an immunopotentiator to a host which program is substantially-free of the tribulations known to the prior art.

Another object of the present invention is to provide a method comprising the controlled and continuous administration of an immunopotentiator to a host over a preselected and predetermined period of time for enhancing the immune response.

Yet another object of the invention is to provide a method comprising administering an immunopotentiator at low rates and in low amounts for reducing or eliminating the incidence of irritation and inflammation previously associated with their use while concomitantly potentiating the immune response.

Yet another object of the invention is to provide a method comprising dispensing an immunopotentiator for substantially reducing and eliminating adverse systemic effects such as fever, malaise, and the like.

Still another object of the invention is to provide a method comprising dispensing an immunopotentiator which method allows for a slow absorption within the host and attainment of greater prophylactic and therapeutic immunological activity over time.

Yet still another object of the invention is to provide a method consisting essentially of dispensing an immunopotentiator from a delivery system that limits its contact with local tissues and which method allows for the controlled release from the system that leads to slow absorption within a host and attainment of enhanced preventive and therapeutic immunological activity.

Yet still another object of the present invention is to provide a method for the administration from a device or matrix which serves as a reservoir, and houses therein an immunopotentiator, said immunopotentiator on release from the device or matrix potentiating antibody production, potentiating the immune response against an impending infection or potentiating the immune response against a disease in progress.

These and other objects of the invention will become more apparent from the following detailed description and the accompanying claims.

SUMMARY OF THE INVENTION

This invention concerns the administration to a host of an immunopotentiator in an effective amount for enhancing the immune response against an impending disease, or a disease in progress. The immunopotentiator is administered at a controlled and predefined rate from a delivery system for a prolonged and determined period of time with an accompanying increased immunologic efficacy and a reduction in the expected side effects, including fever and inflammatory response. The delivery systems used for administering the immunopotentiator include diffusional, osmotic, elastomeric, mechanical or electrical facilitated devices, nonerodible and erodible systems.

DETAILED DESCRIPTION OF THE INVENTION

In accordance with the practice of the present invention, it has now been found that an immunopotentiator can be continuously administered from a delivery system in extremely low to low doses over a prolonged period of time for enhancing the immune response.

Further, in accord with the practice of the invention, the term immunopotentiator is used herein, generically embraces pharmaceutically acceptable and therapeutically acceptable naturally occurring and synthetic materials, representing, originating from, or simulating microorganisms, or their components, as well as materials of plant and animal origins, and their purified or simulated components, organic compounds, and inorganic compounds, that are capable of potentiating specific and non-specific immune response, increasing a host's resistance to an impending infection or disease in progress. The immunopotentiators possess pharmacological activity, that is, they are immunostimulatory agents that broadly enhance the immune response of a host leading to nonspecific immunity, for prophylaxis and defense, or they lead to the development of an increased specific immune response to an antigenic material already present in a host, for improved therapy in case of a preexisting disease.

Exemplary immunopotentiators that can be dispensed according to the mode and manner of the invention generically include a member selected from the group consisting essentially of proteins, lipoproteins, phospholipids, polysaccharides, lipopolysaccharides, peptiolosaccharides, pepticloglycolipids, synthetic organic compounds, biological organic compounds, inorganic compounds, and the like.

More particularly, exemplary immunopotentiators that can be dispensed according to the practice of the invention, specifically include lipopolysaccharides (LPS) extracted from gram-negative bacteria such as Bordetella pertussia or Escherichia coli and the like, immunopotentiators obtained from anaerobic coryneforms, water soluble immunopotentiators obtained from the cell walls of bacteria especially from Calmette-Guerin bacillus, (BCG), immunopotentiators especially cord-factor extracted from mycobacteria, peptidoglycans, peptidoglycans containing an arabinoglactan, peptidoglycolipids containing alanine, glutamic and diamino pimelic acids, water-soluble immunopotentiators(WSA) isolated from cell walls and whole bacteria, e.g. of the species. M. smegmatis, mucopeptides, immunopotentiators obtained from Bacillus subtilis, Saccharomyces cerevisiae, Listeria monocytogenes, Escherichia coli, immunopotentiating proteins of animal origin, immunopotentiating glycopeptides, N-acetylglucosamine derivatives, N-acetyl-muramyl-L-alanyl-D-isoglutamine, lipid A, lysolecithin analogues, polyanions, poly I:C, poly A:U, poly A, poly U, saponin, levamisole, tilorone, lentinan, thymic factor, lymphokines affecting cellular response only, immunopotentiators affecting humoral responses only, immunopotentiators affecting phagocytic response only, immunopotentiators affecting lymphocytic trapping only, nonimmunogenic immunopotentiators, and other immunopotentiators prepared synthetically or derived from the endocrine or derived from the lymphoid or from the reticuloendothelial systems, or otherwise found in animal organisms, and the like pharmaceutically acceptable immunopotentiators. The immunopotentiators are known to the art in *Immunological Adjuvants,* Report of WHO, Geneva 1976, *Biochemical and Biophysical Research Communications,* Ellouz et al, Vol. 59, No. 4, pages 1317 to 1325, 1974; *Agents and Actions,* Bruley-Rosset et al, Vol. 6, pages 251 to 255, 1976; *Chemical Abstracts,* Vol. 88, 136982 to 136985, and 191481, 1978; *Bibliotheca tuberculosea,* Freund, Fasc. 10, pages 130 to 148, 1956; *The Antigens,* Borek, Vol. 4, Chapter 6, pages 369 to 427, 1977; and the references cited therein.

The potentiating effects of selected immunopotentiating agents on the immune system is exemplified by increase in macrophage activity by administering to a host a member selected from the group consisting of C. parvum, B. pertussis, pyran, BCG other mycobacteria, levamisole, polyribonucleotides, and glucan; improves T cell responses by administering a member selected from the group consisting of levamisole, BCG-Freund's complete adjuvant, and B. pertussis; increase in B cell responses by administering a member selected from the group consisting of pyran, glucan, C. parvum, B. pertussis, endotoxins, Bordetella, mycobacterium, retinol BCG-Freund's adjuvant, and tilorone; increase in complement activity by administering levamisole or zymosan; and induce interferon production by administering a member selected from the group consisting of pyran, endotoxin, polysaccharides, poly I:C, other polycations, and tilorone. The potentiating effects of immunostimulants are known in the *Fundamentals of Clinical Immunology,* by Alexander and Good, 1977; in *Scot. Med. J.,* by Howard, Vol. 6, pages 60 to 82, 1961; and in *Immunopharmacology,* Vol. 3, Ch. 14, Hadden, Delmonte and Oettgen, 1977.

The immunopotentiator can be dispensed from a delivery system to a host per se, or they can be dispensed mixed with a pharmaceutically acceptable carrier. The carriers, when used, are transporting vehicles, they are both physiologically and pharmacologically inert, and they are devoid of immunopotentiating activity. Typical inert, non-toxic carriers include sterile solutions, water, saline, physiologically balanced salt solution, and phosphate buffered saline. The immunopotentiator is administered by the present invention oil-free thereby providing improved immunological therapy, without causing local or systemic irritation to the recipient host as caused by the prior art method of administration.

The term host as used herein denotes an animal, pisces, avian, or reptile. The term animal includes warm-blooded mammals such as primates, and humans; farm animals such as sheep, cattle and goats; household animals such as dogs and cats; sport animals such as horses; laboratory animals such as mice, rats, rabbits and guinea pigs; and zoo animals. The term avians includes birds such as chickens and turkeys.

The phrase "a prolonged period of time" as used herein including delivery periods of at least 12 hours, preferably at least 1 day, and periods up to 380 days, such as 1 day to 380 days, 1 day up to 210 days, and the like. More preferably the phrase includes periods of 1 to 180 days inclusive, with a 1 day to 72 days, and presently preferred periods of 1 to 30 days, 1 to 14 days and 1 to 7 days embraced by the phrase. Periods of intermediate duration are included in the phrase. The phrase also includes periods of pretreatment, wherein an immunopotentiator is administered to a host before exposure to the threat of an impending infection, for example from 1 to 30 days, or 1 to 14 days prior to said exposure. The prolonged period of time also includes the time needed to provide an adequate protection against an impending disease, and it also corresponds to the period of time a threat of an impending infection exists, or a disease is in progress.

The expression "a threat of impending infection" denotes an advancing or anticipated epidemic such as cholera, influenza, poliomyelitis, or rubella; childhood infections such as cytomegalovirus, measles, diptheria, poliomyelities, mumps or rubbella; infections prevalent in the environment into which the host is about to enter such as diseases of the tropics including typhoid, cholera, paratyphoid, shigellosis and malaria; infections to which the animal may have been accidentally exposed such as tetanus, rabies and gangrene; diseases such as pneumoccal pneumonia, pseudomonas and bacteroids infections, diseases caused by organisms found abundantly in the environment, but occuring mainly in compromised hosts, and the like. The expression "a disease in progress" denotes a disease such as herpes simplex, rabies, hepatitis, malaria, and the like.

The immunopotentiator composition can be administered in controlled and continuous dosage amounts for producing local and systemic response. The routes of administration include the conventional routes such as intramuscular, subcutaneous, ear intraperitoneal, nasal, ocular, vaginal, transdermal, and the alimentary tract including oral and ano-rectal admission. For preferential local response, the route of introduction can be preselected accordingly. For example, the oral route is indicated for animals including humans where the purpose is to specifically activate the gastrointestinal tract against the threat of diseases for which this is the major or exclusive route of infection, such as poliomyletitis, $E.$ $coli$ $enteritis,$ salmonellosis, typhoid fever, shigellosis, cholera, coccidiosis, and similar diseases. The intramuscular route is indicated for animals threatened with exposure or previously exposed to diphtheria toxoid, tetanus influenza virus, hepatitis virus, herepes simplex virus, salmomella, rhino virus and the like, and in animals challenged with Newcastle disease virus, anaplasma, blackleg, and the like. Routes of administration and body passageways are disclosed in $The$ $Merck$ $Veterinary$ $Manual,$ 4th Edition, 1973; and in Topley and Wilson's $Principles$ $of$ $Bacteriology$ $and$ $Immunology,$ Vols. I and II, 1975.

The expression "delivery system" as used herein denotes a system or delivery means that can deliver a therapeutically effective amount of an immunopotentiator for producing an immune response in a preselected host. The systems are a means for delivering the immunopotentiator, and the systems include reservoir means for housing the immunopotentiator. Generally, the reservoir is an integral part of the system, and in an embodiment, a delivery means can be connected to a reservoir housing the immunopotentiator. The systems used do not allow for the total and complete direct access of cellular or humoral tissues and fluids of the animal to all the immunopotentiator in the system. This limited contact and substantial lack of interaction between the system and the agents housed therein with the tissues and fluids of the hosts, coupled with the presently preferred extremely slow administration of often potentially harmful immunopotentiators, significantly reduces and prevents incidence of local inflammation, or adverse biological response such as fever or malaise. The systems can be used parenterally, subcutaneously, intramuscularly, orally, anorectally, and the like. The systems can be an external system carried by the host, which administers the immunopotentiator via a catheter to the host, for example, through the catheter directly or connected to a needle implanted subcutaneously, intramuscularly, or intravenously. The use of these system does not cause local inflammation, and they can be internally implanted biocompatible systems that release the immunopotentiator at an effective and controlled rate.

The delivery systems can house from 1 ng to 10 g of immunopotentiator for administering it subcutaneously, intramuscularly, and to like immunopotentiator receptive sites over a prolonged period of time. The amount of immunopotentiator released from the delivery systems is an effective amount for producing an immune response, usually from 1 pg to 5000 mg per day, more preferably from 10 pg to 100 mg per day, and still more preferably from 0.1 ng per hr. to 1000 ng per hr. Doses of immunopotentiator outside these ranges can be administered whenever they will lead to an immune response and continuous administration in this range can be used insofar as they will usually maintain the response.

The delivery systems can be bioerodible or non-erodible. Representative bioerodible systems include systems shaped like an implant of any geometric spatial configuration, and presenting the appearance of square, rectangle, disk and the like, housing the immunopotentiator. The bioerodible systems are made of release rate controlling materials that act as a reservoir and expose the biological environment to non-toxic ends products as the systems erode with the concurrent release of the immunopotentiator. The bioerodible system usually house from 1 ng to 5 g of immunopotentiator for release over the preferred period. Representative bioerodible polymers suitable for manufacturing the immunopotentiator delivery systems include poly(carboxylic acid) as disclosed by Heller et al in U.S. Pat. No. 3,811,444; polyvalent cross-linked polyelectrolytes as disclosed by Michaels in U.S. Pat. No. 3,867,519; polyesters, polylactic and polyglycolic acids as disclosed by Ramwell in U.S. Pat. No. 3,887,975; poly(ethylene oxide), poly(acrylamide), poly(vinyl pyrrolidone), copolymeric polysaccharides, poly(vinyl imidazole), poly(vinyl alkyl ether), and poly(alkyl aldehyde) as disclosed by Zaffaroni in U.S. Pat. No. 3,971,367; poly(methacrylamide) and copolymers of acrylamide and methacrylamide as disclosed by Ramwell in U.S. Pat. No. 3,993,057; poly(orthoesters) and poly(orthocarbonates) as disclosed by Choi et al in U.S. Pat. No. 4,138,344; poly(N-acetylglucosimines) as disclosed by Capozza in Belgium Pat. No. 825,367; and the like.

Representative delivery systems that maintain their physical and chemical integrity during the administration of an immunopotentiator included non-erodible systems such as the osmotic powered device disclosed by Theeuwes in U.S. Pat. No. 3,760,984; the osmotic dispensing device as disclosed by Theeuwes et al in U.S. Pat. No. 3,916,899; the electroosmotic pump as disclosed by Theeuwes in U.S. Pat. No. 3,923,426; the diffusion powered device as disclosed by Zaffaroni in U.S. Pat. No. 3,993,072; the osmotic miniature pump as disclosed by Higuchi in U.S. Pat. No. 3,995,631; the infusion apparatus as disclosed by Buckles et al. in U.S. Pat. No. 4,410,117; the Harvard infusion pump; and the like. The devices include reservoir means and they can be implanted in the host, introduced into the host through body openings such as the ano-rectal route, the oral route, the vaginal route, or they can be carried exteriorly by the host with a tube that conveys the immunopotentiating agent from the device to the host.

The immune response, its intensity and the extent thereof produced by the method of the invention can be ascertained by measuring antibodies in the plasma by standard techniques. Additional techniques that can be used for ascertaining the nature of the provoked response include measuring active physiological reactions, such as skin reactions following topical subdermal or intradermal antigen administration, and by measuring the degree of inhibition of toxic response. More peertinent measures for the purpose of this invention include phagocytic index, macrophage enzyme activity, concentration of complement factors, protection from experimental bacterial, viral, fungal and parasitic infections, and particulate clearance from blood. These techniques and other acceptable techniques are known to the art in *Fundamentals of Immunology,* by Weiser et al., 1972, published by Lea & Febiger; in *Immunology* by Bellanti, 1971, published by W. B. Saunders Co.; in *Practical Immunology,* by Hudson et al., 1976, published by Blackwell Scientific Publications; in *Essential Immunology* by Roitt, 1974, published by Blackwell Scientific Publications; *Handbook of Experimental Immunology,* by Weir, 1973, published by Blackwell Scientific Publications; and in *The Macrophage,* by Pearsall et al., 1970, published by Lea & Febiger Co.; which publications are incorporated herein by reference.

The following examples are merely illustrative of the present invention and they should not be considered as limiting the scope of the invention in any way, as these and other examples and equivalents thereof will become more apparent to those versed in the art in the light of the present disclosure, and the accompanying claims.

EXAMPLE 1

In this example, the coadministration of lysozyme and lipopolysaccharide at a controlled and continuous rate is compared with lysozyme alone in animals. The composition of lysozyme and lipolysaccharide were administered from a device comprised of an elastomeric reservoir made of butyl rubber surrounded on its exterior surface by a layer of the osmotic solute sodium chloride, and an outer layer of semipermeable cellulose acetate. The same device was used for administering the lysozyme alone. The osmotic devices used for administering the substances were made according to U.S. Pat. No. 3,995,631.

In the studies, the lysozyme used was hen egg lysozyme, the immunopotentiator was lipopolysaccharide derived from E. Coli, and the animals were Swiss-Webster male mice weighing about 33 g, and continuous delivery was achieved by implanting the osmotic delivery systems subcutaneously.

The antibodies were assayed by a modified Farr assay. This method measures the amount of radioactive antigen bound by the antibody contained in the test serum. The test was performed at an antigen concentration of 100 ng/ml by mixing 100 ml of antigen solution, 200 ng antigen/ml, with an equal volume of various dilutions of the test serum. The results are expressed as $\mu$g lysozyme bound per ml of the undiluted serum.

The study was designed to compare the amount of antibody produced by immunizing with lysozyme delivered at a controlled and continuous rate over a prolonged period of time without immunopotentiating agent, with the amount of antibody produced in mice immunized with identical doses of the antigen with immunopotentiator.

Two groups of mice, with 7 mice in a group, were immunized, and the animals bled for antibody titration 14, 28 and 60 days after initiation. The potentiation of antibody production by simultaneous administration of antigen and immunopotentiator in soluble form by controlled continuous delivery over a prolonged period of time is given in Table I. In the table LY indicates lysozyme and LPS indicates lipopolysaccharide

TABLE I

| GROUP | GROUP Wt. g | IMMUNIZATION | $\mu$g LYSOZYME BOUND/ml SERUM AT DAYS | | |
|---|---|---|---|---|---|
| | | | 14 | 28 | 60 |
| I | 234 | 10 $\mu$g Ly 4 WCD | 0.87 [0.42–2.31] | 5.50 [0.6–9.4] | 1.13 [0.44–2.70] |
| II | 233 | 10 $\mu$g Ly + 100 $\mu$g LPS 4 WCD | 1.65 [0.43–2.93] | 16.2 [3.35–35.0] | 3.48 [1.09–8.20] |

The osmotic device used for administering the immunological agents in Example 1 comprised an elastomeric reservoir made of butyl rubber surrounded by a layer of osmotic solute sodium chloride and an outer layer of cellulose acetate. The device was made according to U.S. Pat. No. 3,995,631. This device was also used in Examples 2, 3 and 4. In the tables CD indicates continuous delivery, WCD indicates weeks of continuing delivery, and MP indicates the osmotic device just described and made as a pump for implanting in a host.

EXAMPLE 2

In this example, the coadministration of the antigen tetanus toxoid and the immunopotentiator lipopolysaccharide administered for 4 weeks is compared with the results of single injection.

The assay of immunity was performed using the toxin challenge method as follows: graded doses of tetanus toxin diluted in $PO_4$ buffered saline containing 0.25% bovine serum albumin, BSA, were injected in 0.5 ml volume into each mouse subcutaneously. The mice were Swiss-Webster, female, weighing about 26 g. Mice were observed for symptoms of Tetanus, and death times were recorded. The periods of observation were as follows: 30-40 hours every 2 hours, 40-66 hours for every four hours, and 84 to 200 hours every 24 hours.

challenged with 8, 20, 50 or 125 MLDs. The results for the immunopotentiating effect of continuous administration of tetanus toxoid with or without lipopolysaccharide are given in TABLE II.

TABLE 2

| GROUP | IMMUNIZATION TOXOID | LPS µg | Adm. | CHALLENGE DOSE OF TOXIN in MLDs (1) | | | | | CALCULATED LETHAL DOSE OF TOXIN (in MLD) | IU/ml (2) Pooled Serum |
|---|---|---|---|---|---|---|---|---|---|---|
| | | | | 1 | 8 | 20 | 50 | 125 | | |
| I | 0.1 Lf | NIL | | | | ¼ | 0/4 | | >50 | 0.10 |
| II | | 0.2 | | | | 0/3 | ¼ | | >50 | 0.10 |
| III | | 1.0 | 4W | | | | 0/3 | 0/4 | >125 | 0.24 |
| IV | | 5.0 | | | | | 0/3 | 2/4 | >125 | 0.40 |
| V | | NIL | | | 45 ± 8 | 48 ± 25 | | | <8 | |
| VI | | 0.2 | | | ¼ | 164 ± 11 | | | 20 | 0.02 |
| VII | | 1.0 | Sc. | | ¾ | 65 ± 33 | | | <20 | |
| VIII | | 5.0 | Inj. | | | ¼ | 62 ± 34 | | <50 | 0.03 |
| IX | | 20.0 | | | | | 33 ± 3 | 31 ± 2 | ~1 | |
| X | | Unimmunized Control | | 146 ± 30 | 38 ± 5 | 32 ± 3 | | | 1 | |

In Table 2 the footnotes are as follows:
(1) Response to toxin challenge: where all the mice died of challenge, the geometric death time (± SE) is given, otherwise the data are expressed as the number of mice dead in ± 200 hours/the number of mice challenged.
(2) International Units per ml of pooled serum, as compared to Connaught Laboratories Laboratory Standard.

The immunity was expressed as the number of minimum lethal doses of toxin required to kill immunized mice. The minimum lethal dose, MLD, is defined as the minimum dose of Toxin which kills all challenged mice in 200 hours or less.

The antitoxin titration was performed as follows: equal volumes of toxin and doubling dilution of antisera were mixed, incubated at 37° C. for 1 hr. and injected subcutaneously in 0.5 ml volume into normal mice. Three mice were tested at each dilution of antiserum. The potency of the test sera were assayed in comparison with the standard tetanus antitoxin, tested in parallel with the test sera. The antitoxin titrations were carried out at 1+/400 levels, that is, the dose of toxin injected into each mouse was such that when mixed with 1/400 units of the standard antitoxin, the mixture killed the mice in 168 hours.

The experiment compares the immunopotentiating effect of lipopolysaccharide given simultaneously with antigen in a single injection with the immunopotentiating effect of lipopolysaccharide given simultaneously and continuously with antigen for four weeks. The antigen used, tetanus toxoid, permitted the use of an in vivo assay, with neutralization of toxin, for measuring the immunopotentiating effect.

Nine groups of mice (7/group) were immunized with a constant dose of tetanus toxoid (0.1 Lf=0.3 g) mixed with graded doses of LPS. Five of the groups received the immunizing dose of LPS and antigen, or antigen alone by a single subcutaneous injection. The immunizing dose was administered to the other 4 groups for 4 weeks, 4W. Twenty-eight days after the initiation of immunization, all mice were bled for antitoxin titration. On day 33, 3 mice from each group were challenged with 20 or 50 minimum lethal doses of tetanus toxin, and on day 35, the remaining 4 mice from each group were

EXAMPLE 3

In this example, the immunopotentiator was administered either over the first few days only, or throughout the total administration period, and the immunopotentiating effect was measured by antibody titer 30 days after the initiation of the administration.

Three groups of Swiss-Webster mice, 10 per group, were used in the study. Groups I and II were immunized with tetanus toxoid, with or without LPS, lipopolysaccharide adminstered in two tiers. In group I, the first tier was administered, without LPS, via a single subcutaneous injection on day zero, in group II, the first tier was administered with LPS via a continuous delivery miniature pump over a period of 3 days. The mice in group III were immunized with tetanus toxoid and LPS administered continuously through a 4 week miniature pump. In this experiment, therefore, a single tier administration is applied.

On day 32 the mice were bled and the antitoxin content of the pooled serum was determined at the L+/500 level.

On day 39-41, mice in groups of 3-4 were challenged with 125, 250 and 500 MLDs of tetanus toxin.

The results of the study are presented in Table 3. At days 30-40 after immunization, equivalent levels of immunity (as measured by the toxin challenge method or the antitoxin neutralization method) were achieved when either antigen alone, or antigen and immunopotentiator were administered by the two tiered pattern. The continuous coadministration of antigen and immunopotentiator as in group III was significantly more effective. This indicates the effective prolonged action of the immunopotentiator, administered at very low rates.

TABLE 3

| | IMMUNIZATION | | | | | | ANTI-TOXIN (IU/ml) ON DAY 32 | TOXIN CHALLENGE ON DAY 39-41[1] | | |
|---|---|---|---|---|---|---|---|---|---|---|
| | 1st TIER | | | 2nd TIER | | | | MLD | | |
| GROUP | TOXOID (Lf) | LPS (µgs) | ADMINIS-TRATION | TOXOID (Lf) | LPS (µgs) | ADM | | 125 | 250 | 500 |
| I | 0.05 | — | Sc. Inj | 0.05 | — | 4 WMP | 0.16 | 0/3 | ¼ | 21 |
| II | 0.05 | 0.2 | 3 DMP | 0.05 | — | 4 WMP | N.D. | ¼ | ¼ | 34 |

TABLE 3-continued

| GROUP | IMMUNIZATION | | | | | | ANTI-TOXIN (IU/ml) ON DAY 32 | TOXIN CHALLENGE ON DAY 39-41[1] MLD | | |
|---|---|---|---|---|---|---|---|---|---|---|
| | 1st TIER | | | 2nd TIER | | | | | | |
| | TOXOID (Lf) | LPS (µgs) | ADMINIS-TRATION | TOXOID (Lf) | LPS (µgs) | ADM | | 125 | 250 | 500 |
| III | NIL | | | 0.1 | 0.2 | 4 WMP | 0.32 | 0/3 | 0/4 | ⅜ |

In Table 3, WMP means weeks administered by a miniature pump. The footnote indicator 1 denotes the results of toxin challenge: where all mice challenged with a given dose of toxin died in 200 hrs., the geometric mean death time is given; otherwise the response to challenge is expressed as the number of mice died in 200 hrs/no. of mice challenged.

EXAMPLE 4

This example evaluates the dependence of the immunopotentiating effect on the continued administration of the immunopotentiator. The immunopotentiator was administered continuously with the antigen over a period of 5 weeks or for a period of one week only; in the latter case, only antigen was administered during the succeeding 4 weeks.

The composition of antigen and immunopotentiator or antigen alone were administered from a device comprised of an elastomeric reservoir made of butyl rubber surrounded on its exterior surface by a layer of the osmotic solute sodium chloride, and an outer layer of semipermeable cellulose acetate. The osmotic devices used for administering the substances were made according to the U.S. Pat. No. 3,995,631.

In these studies, the antigen was diphtheria toxoid and the immunopotentiator was lipopolysaccharide derived from E. coli and the animals were Swiss-Webster male mice weighing about 30 gms. Controlled delivery of antigen with or without immunopotentiator was achieved by implanting two osmotic delivery systems/mouse, in sequence. The first system delivered antigen and immunopotentiator for a period of 1 week. The second system delivered antigen with or without immunopotentiator for 2-5 weeks.

The antibodies were assayed by a modified Farr assay. The results were expressed as Lf diphtheria toxoid bound per ml of serum.

This study was designed to compare the immunopotentiating effect of lipopolysaccharide delivered at a controlled and continuous rate with the antigen for a period of 5 weeks with the immunopotentiating effect achieved with the same amount of LPS administered with the antigen continuously for a period of one week only. In both instances, an identical amount of antigen was administered for a period of 5 weeks.

Two groups of mice, with 8 mice per group, were immunized as described above and bled for antibody titration on days 8, 15 and 35. The potentiation of antibody production by continuous administration of antigen and immunopotentiatior is given in Table 4. In the Table DT indicated diphtheria toxoid and LPS indicates lipopolysacharide. The same dose of LPS (10 mcg) is more effective when given continuously over a period of 5 weeks than when administered over a period of 1 week only.

TABLE 4

| GROUP | GROUP WT | IMMUNIZATION | | Lf DT bound/ml serum on Days | | |
|---|---|---|---|---|---|---|
| | | WEEK = 1 | WEEK = 2-5 | 8 | 15 | 35 |
| I | 240 | DT = 3 Lf LPS = 10 mcg | DT = 2 Lf LPS = NIL | .20 | 1.49 | 5.74 |
| II | 238 | DT = 3 Lf LPS = 2 mcg | DT = 2 Lf LPS = 8 mcg | .20 | 3.12 | 13.30 |

The above studies indicate that a method of administering an immunopotentiator over a prolonged period of time at low concentrations lead to enhancement of the antibody response, and they thus show the potentiating activity of the immunopotentiator activity over that period of time for which it is administered to the host. In these studies, an antigen was used to quantify the immune response and they evidenced immunostimulating activity by ensuring antibody production. Concomitantly, it becomes evident in the light of the present invention, that the immune response against any infectious agent encountered by the host while receiving the immunopotentiator alone will be similarly potentiated. While certain studies have been set forth in detail above, albeit more complex studies can be used to demonstrate the persistence and enhancement of the immunopotentiating effects. That effective immunostimulants can active phagocytosis activity in animals for nonspecific protection against infection, or a disease in progress is known in the following references: J. Exp. Med., Jenkins et al. Vol. 112, pages 419 to 429, 1960; J. Bacteriol., Ranson et al. Vol. 84, pages 466 to 472, 1962; Science, Wooles et al, Vol. 142, pages 1078 to 1080, 1963; Hebd. Seances. Acad. Sci., Parant et al., Vol. 260, pages 2630 to 2633, 1965; Nat. New Biol., Adlam et al., Vol. 235, pages 219 to 220, 1972; Proc. Nat. Acad. Sci., Fauve et al., Vol. 71, pages 573 to 577, 1974; Lancet, Versijp et al, Vol. 1, No. 7910, page 798, 1975; Proc. Nat. Acad. Sci., Chedid et al., Vol. 74, pages 2089 to 2093, 1977; in U.S. Pat. No. 4,083,987 Bicher et al., U.S. Pat. No. 4,153,684, Audibert et al., in Bacterial Endotoxins, Ed. by Landy, 1964, published by Quinn & Boden Co., Rahway N.J.; and Principles of Bacteriology and Immunology, by Topley and Wilson, Vol. I and II, 1975, published by Williams & Wilkens Co.

While the invention has been described and illustrated with details and references to certain preferred embodiments, those skilled in the art will appreciate that various modifications, changes, omissions, and substitutions can be made without departing from the spirit of the invention.

We claim:

1. A method for potentiating the immune response of a host, which method consists essentially of administering to a host needing potentiation of the immune response an immunopotentiating agent, said agent administered from a therapeutic delivery system that limits the contact of the host with the agent until the agent is released oil-free from the system, thereby lessening the incidence of local inflammation, fever and adverse biological response of the host to the agent, which agent is administered in a therapeutically effective amount of at least one picogram for a prolonged period of time of at least 12 hours for potentiating the immune response.

2. The method potentiating the immune response of a host according to claim 1, wherein the host is a warm-blooded animal, and the method comprises administering the immunopotentiating agent to the animal to potentiate the immune response of the animal against an impending infection.

3. The method for potentiating the immune response of a host according to claim 1, wherein the host is a warm-blooded animal, and the method comprises administering the immunopotentiating agent to the animal for potentiating the immune response of the animal against a disease in progress.

4. The method for potentiating the immune response of a host according to claim 1, wherein the host is an animal, the prolonged period of time corresponds to the period of a threat of an impending infection and the immunopotentiating agent produces a nonspecific immune response.

5. The method for potentiating the immune response of the host according to claim 1, wherein the prolonged period of time is at least 1 day up to 380 days.

6. The method for potentiating the immune response of the host according to claim 1, wherein the host is a human.

7. The method for potentiating the immune response of the host according to claim 1, wherein the host is an animal, the immunopotentiator is nonimmunogenic and mixed with a pharmaceutically acceptable carrier, and the mixture is administered in a prophylactically effective amount at a controlled and continuous rate for up to 180 days to potentiate the immune response against an infection.

8. The method for potentiating the immune response of the host according to claim 1, wherein the therapeutic delivery system is a matrix and the immunopotentiating agent is housed in the matrix, which matrix is formed of a nontoxic, bioerodible material that bioerodes at a controlled and continuous rate over a prolonged period of at least 1 day up to 180 days, thereby administering the immunopotentiating agent to the host at a controlled and continuous rate over a period of at least 1 day up to 180 days.

9. The method for potentiating the immune response of the host according to claim 1, wherein the therapeutic delivery system comprises a reservoir, and the immunopotentiating agent is administered at a controlled rate in a therapeutically effective amount for potentiating the immune response from the reservoir of an external therapeutic delivery system to the host.

10. The method for potentiating the immune response of the host according to claim 1, wherein the therapeutic delivery system is positioned in the host and the method comprises administering a biologically acceptable immunopotentiating agent at a controlled rate and in a therapeutically effective amount for potentiating the immune response from said delivery system.

11. The method for potentiating the immune response of the host according to claim 1, wherein the therapeutic delivery system is used in a single application and limits contact of the host with the agent until it is administered to the host, and wherein the method comprises the controlled and continuous delivery of the immunopotentiating agent from the system to the host over a prolonged period of 1 to 180 days.

12. The method for potentiating the immune response of the host according to claim 1, wherein the therapeutic delivery system comprises an internal reservoir and the immunopotentiating agent is housed in the reservoir that limits the agent's contact with the tissues and fluids of the host until the agent is released from the delivery system.

13. The method for potentiating the immune response of the host according to claim 1, wherein the therapeutic delivery system is an osmotic delivery system.

14. The method for potentiating the immune response of the host according to claim 1, wherein the therapeutic delivery system is a diffusional delivery system.

15. The method for potentiating the immune response of the host according to claim 1, wherein the method produces an early appearance of an immune response high enough to protect the host from an immediate threatening infection.

16. The method for potentiating the immune response of the host according to claim 1, wherein the host is a warm-blooded animal, and the immunopotentiator potentiates the immune response of the gastrointestional tract against a disease that enters the tract.

17. The method for potentiating the immune response of the host according to claim 1, wherein the host is warm-blooded animal and the therapeutic delivery system administers the immunopotentiating agent intramuscularly to produce the desired effect.

18. The method for potentiating the immune response of the host according to claim 1, wherein the host is a warm-blooded animal and the therapeutic delivery system administers the immunopotentiating agent subcutaneously to produce the desired effect.

19. The method for potentiating the immune response of the host according to claim 1, wherein the host is a warm-blooded animal and the therapeutic delivery system administers the immunopotentiating agent parenterally to produce the desired effect.

20. The method for potentiating the immune response of the host according to claim 1, wherein the host is a warm-blooded animal and the therapeutic delivery system administers the immunopotentiating agent parenterally to produce the desired effect.

21. The method for potentiating the immune response of the host according to claim 1, wherein the prolonged period of time comprises a period of time prior to exposure of the host to a disease.

* * * * *